United States Patent [19]
Schwab

[11] Patent Number: 5,437,640
[45] Date of Patent: Aug. 1, 1995

[54] APPARATUS AND METHOD FOR INSERTING HYPODERMIC, TUBERCULIN AND OTHER NEEDLES AND FOR ADMINISTERING MANTOUX TUBERCULIN TESTS

[76] Inventor: Louis Schwab, 310 Orton Rd., Yellow Springs, Ohio 45387

[21] Appl. No.: 189,452

[22] Filed: Jan. 31, 1994

[51] Int. Cl.⁶ .................... A61M 5/32; A61M 5/42
[52] U.S. Cl. ........................ 604/116; 604/180
[58] Field of Search ............ 604/115, 116, 174, 180; 606/172

[56]     References Cited
     U.S. PATENT DOCUMENTS

| | | | |
|---|---|---|---|
| 1,125,887 | 1/1915 | Schimmel . | |
| 1,436,707 | 11/1922 | Gaschke | 604/117 |
| 2,091,438 | 8/1937 | Epstein | 604/117 |
| 2,198,666 | 4/1940 | Gruskin . | |
| 2,238,323 | 4/1941 | Hollingsworth . | |
| 2,451,183 | 10/1948 | Tantimonaco . | |
| 3,167,072 | 1/1965 | Stone et al. . | |
| 3,683,911 | 8/1972 | McCormick | 604/180 |
| 3,920,001 | 11/1975 | Edwards | 604/180 |
| 4,170,993 | 10/1979 | Alvarez . | |
| 4,235,234 | 11/1980 | Whitney et al. . | |
| 4,332,298 | 6/1982 | DeVitis | 604/180 |
| 4,408,611 | 10/1983 | Enjoji | 604/116 |
| 4,497,325 | 2/1985 | Wedel | 604/116 |
| 4,572,182 | 2/1986 | Royse | 604/116 |
| 4,586,924 | 5/1986 | Lanning | 604/115 |
| 4,645,492 | 2/1987 | Weeks | 604/174 |
| 4,666,434 | 5/1987 | Kaufman | 604/179 |
| 4,857,058 | 8/1989 | Payton . | |
| 4,865,590 | 9/1989 | Marmar . | |
| 5,100,387 | 3/1992 | Ng . | |
| 5,167,629 | 12/1992 | Vertenstein et al. . | |

FOREIGN PATENT DOCUMENTS

461457  6/1928  Germany ............................ 604/116

Primary Examiner—Paul J. Hirsch
Attorney, Agent, or Firm—Wood, Herron & Evans

[57]     ABSTRACT

A device for guiding the insertion of a hypodermic, tuberculin or other needle and, more particularly for administering a Mantoux tuberculin test is disclosed comprising a platform having a channel extending therethrough sized to receive a flexible needle for guiding the insertion of the needle at a prescribed angle, direction and depth for the introduction or removal of fluids from the body.

39 Claims, 3 Drawing Sheets

APPARATUS AND METHOD FOR INSERTING HYPODERMIC, TUBERCULIN AND OTHER NEEDLES AND FOR ADMINISTERING MANTOUX TUBERCULIN TESTS

FIELD OF THE INVENTION

The present invention relates generally to devices for guiding the insertion of a sterile hypodermic, tuberculin or other needle into the body at a prescribed angle, direction and depth for the introduction or removal of fluids from the body and, more particularly, to devices and methods for introducing a tuberculin needle into the epidermis for easy and accurate administration of a Mantoux tuberculin test.

BACKGROUND OF THE INVENTION

The need for accurate and repeatable insertion of sterile needles, such as hypodermic, tuberculin or other needles, is a problem frequently encountered in many medical procedures. This accuracy is particularly necessary in performing tuberculin tests.

For many years, beginning in the early 1900's, an intradermal skin test had been used to detect the presence of tuberculin sensitivity in a test subject. This intradermal test, known as the "Mantoux Test," involved injecting a measured amount of proteins derived from the tubercle bacillus, the organism responsible fir tuberculosis, into the epidermis of the test subject. A positive test, indicated by swelling and redness at the injection site, provided evidence that the test subject had been exposed to the tubercle bacillus and established a presumptive diagnosis of clinical tuberculosis.

Although the intradermal Mantoux tuberculin test is highly reliable when correctly performed, it is difficult to administer accurately as it requires the insertion of the needle into the epidermis, the thin outer layer of the skin, and not into the dermis, the deep layer of skin. This necessitates inserting the needle at a very shallow angle, which is difficult to perform, even for the most skilled operators.

About twenty years ago a simplified tuberculin test, the "tine test", was developed. In this test, a small plastic button having multiple sharp tines projecting from the base of the button is used. The tines are coated with a dried tuberculin solution that, in theory, deposit a standard amount of tuberculin test material at a standard depth below the surface of the skin. Recently, the tine test has been proven to be inaccurate and infectious disease authorities are considering recommending that it be abandoned in favor of the original Mantoux tuberculin test. However, a whole generation of physicians and nurses are now unfamiliar with the test. Further, the accuracy required in administering the Mantoux Test makes it difficult to quickly and reliably perform, particularly by non-physicians.

Thus, there has been a considerable need for a device and method for reliably, repeatedly and quickly inserting a needle into the body of a person at a desired angle, direction and depth and, more particularly, for administering a Mantoux tuberculin test.

SUMMARY OF THE INVENTION

The present invention provides a device and method for guiding the insertion of a sterile needle, such as a hypodermic, tuberculin or other needle, at a prescribed angle, direction and depth for the introduction or removal of fluids from the body. More specifically, the sterile needle guide provides a device adapted to quickly, safely and reliably administer a Mantoux tuberculin test. To this end, and in accordance with the principles of the present invention, a platform having a channel extending therethrough is provided. The channel is sized to receive and guide a flexible sterile needle, such as a tuberculin needle, for insertion into the body for introduction or removal of fluids.

To assist in placement of the platform at the needle insertion site, the platform may include a thumb-stop sized to receive the thumb of an operator, and gripping means to grip the skin of the test subject and prevent movement thereof during insertion of the needle. The gripping means may comprise a plurality of serrations and an adhesive strip on the underside surface of the platform.

Where a shallow angle of entry into the body is desirable, such as in administering the Mantoux tuberculin test, the channel in the platform may follow a curvilinear path to give the sterile needle a curvilinear trajectory. This curvilinear path may comprise an initial arcuate path followed by a substantially horizontal segment, thereby causing the needle to enter the skin at a shallow depth and then proceed substantially parallel to the skin surface. Proper selection of the dimensions of the channel results in the needle piercing the skin to a depth just below the surface of the epidermis for insertion of tuberculin test material. Further, the channel may have an inverted triangular cross-section to assist in orienting the needle during the insertion process.

In those applications, such as in a tuberculin test, where a wheal will be formed on the surface of the skin, the platform may include a slot that is positioned above the injection site that is sized to permit formation of the wheal.

To use the sterile needle insertion device, the platform is placed against the skin of the test subject. The operator then pushes downwardly and forwardly on the thumb stop, causing the gripping means to stretch the skin taut. The needle is then introduced into the channel and inserted into the skin to the desired depth or until the hub of the needle contacts the platform. Following the introduction or removal of fluids, the needle is withdrawn and the platform is removed from the test subject's skin.

The sterile needle insertion device may be adapted to provide additional advantages. More specifically, and in accordance with a further aspect of the invention, a sterile needle may be, placed in the channel during construction of the platform. To prevent the tip of the needle from protruding below the lower surface of the platform prior to use, a removable needle stop may be placed over the needle adjacent the hub of the needle. Further, a dry substance to be flushed into the injection site may be deposited within the lumen of the hollow needle during construction. When used for administering the Mantoux tuberculin test, this dry substance would be purified protein derivative (PPD). To use this device, a syringe (that may be empty, contain diluent or contain the fluid to be injected) is attached to the hub of the needle and the needle stop removed from the needle. As before, the platform is placed on the skin of the test subject with the operator pushing downwardly and forwardly on the thumb stop causing the gripping means to stretch the skin taut. The needle is advanced until it is inserted into the skin to the desired depth. Following injection or removal of fluids, the needle is withdrawn and the platform removed from the skin of the test subject.

By virtue of the foregoing, there is thus provided a device and method for easily, safely and reliably inserting a sterile needle into the body at a prescribed angle, direction and depth for the introduction or removal of fluids from the body. More specifically, there is provided a device and method for quickly and reliably administering a Mantoux tuberculin test. These and other objects and advantages of the present invention shall be apparent from the accompanying drawings and the descriptions thereof.

BRIEF DESCRIPTION OF THE DRAWINGS

The accompanying drawings, which are incorporated in and constitute a part of this specification, illustrate embodiments of the invention and, together with a detailed description of the invention given below, serve to explain the principles of the present invention.

DETAILED DESCRIPTION OF THE DRAWINGS

Figures 1, 2, 5:
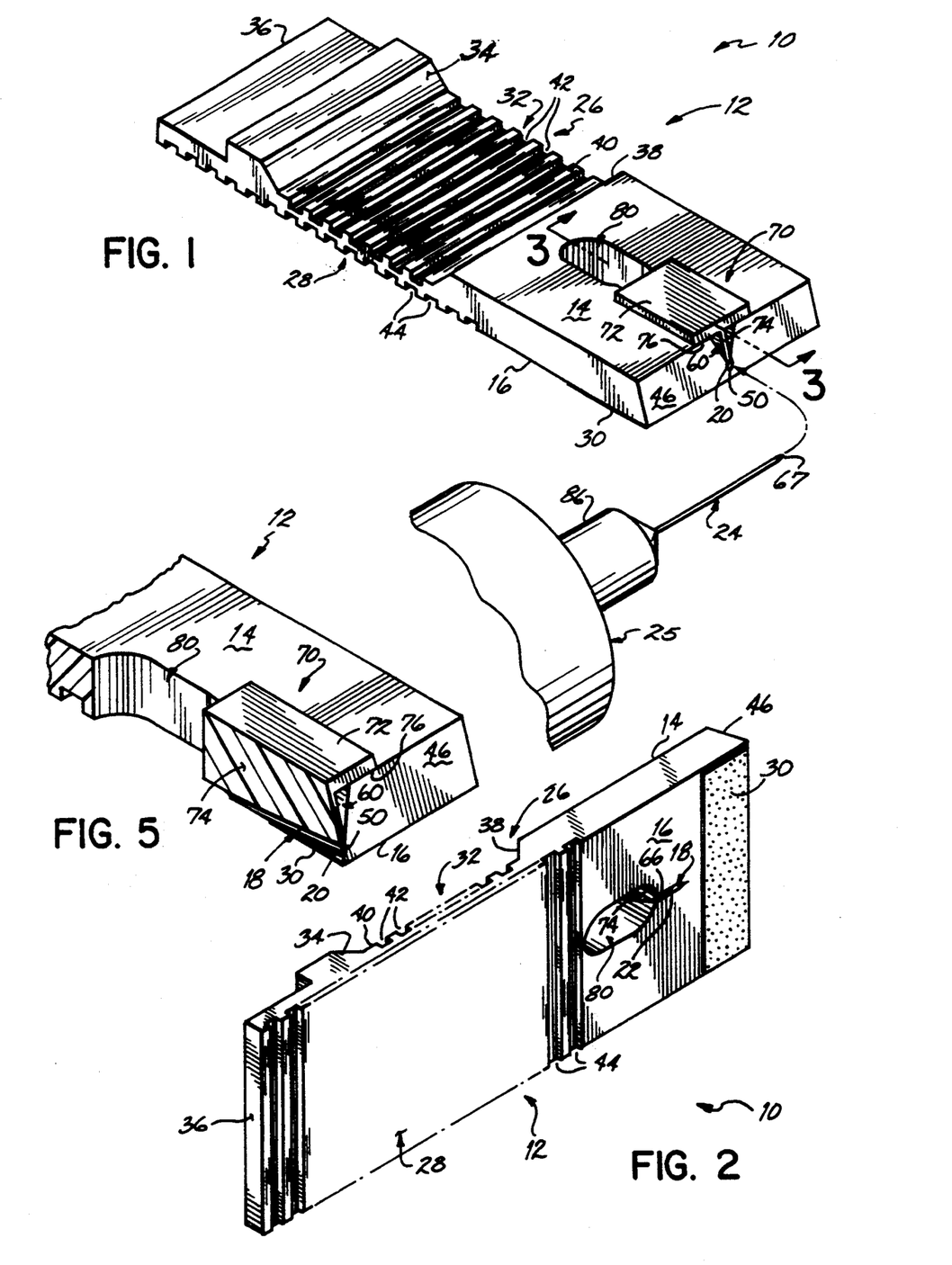
FIG. 1 is a top perspective view of a Mantoux tuberculin test device in accordance with the principles of the present invention.
FIG. 2 is a bottom perspective view of the Mantoux tuberculin test device of FIG. 1.
FIG. 5 is a partial perspective view of the Mantoux tuberculin test device of FIG. 1.
Figure 3:
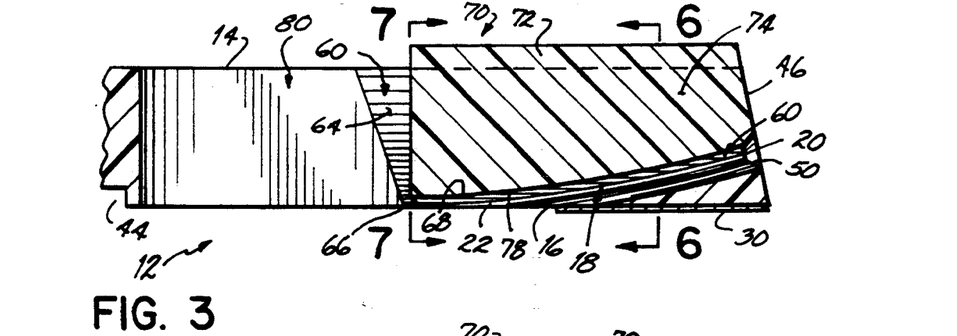
FIG. 3 is a cross-sectional view of the Mantoux tuberculin test device taken along 3—3 of FIG. 1.

With reference to FIGS. 1-3, there is shown a Mantoux tuberculin test administration device 10 comprising a platform 12 having a first side 14 and second opposing side 16 with a channel 18 extending therethrough. Channel 18 has an inlet 20 and an outlet 22 and is sized to receive and guide a hollow sterile needle 24 of a tuberculin syringe 25. Together, platform 12 and channel 18 cooperate to guide the insertion of hollow needle 24 into the body of a person at a prescribed angle, direction and depth for the introduction of tuberculin test material.

Typically, hollow needle 24 is a standard #27 (½ inch) regular bevel needle having a 0.016 inch outer diameter. However, as will be readily apparent to those skilled in the art, tuberculin test device 10 may be modified for use in guiding the insertion of any hollow needle into the body of a person at any site both for introduction of fluids and for removal of fluids from the body. Thus, test device 10 made in accordance with the principles of the present invention may be used in other medical procedures requiring the controlled introduction of sterile needles into the body. These procedures include lumbar punctures, solid organ biopsies, intraarterial aspirations of blood, subdural aspirations of blood, subcutaneous or intramuscular injections (including self-administered injections) of medicines and vaccines and aspiration of urine samples from the bladder of an infant to name but a few. Other applications and procedures to which the present invention may be used will be readily apparent to those skilled in the art.

Platform 12 is preferably a rigid rectangular plate made from plastic having a length of about 1.5 inches to about 1.8 inches, a width of about 0.625 inch to about 0.75 inch and a thickness of about 0.1 inch to about 0.125 inch. It has been found more advantageous for use in administering the Mantoux tuberculin test for platform 12 to have a length of about 1.8 inches, a width of about 0.625 inch and a thickness of about 0.125 inch. However, as will be readily apparent, these dimensions will vary as needed depending upon the type of procedure to which the device is to be applied.

To assist in placing platform 12 at the location where needle 24 is to be inserted, platform 12 includes a thumb stop 26 on first side 14 and grips 28 and an adhesive strip 30 on second opposing side 16. Thumb stop 26 consists of a groove 32 sized to receive the thumb of an operator formed by a front wall 34 that is parallel to and about 0.4 inch behind the leading edge 36 of platform 12, a rear wall 38 about 0.7 inch from from wall 34 and an interconnecting floor 40 that is about 0.06 inch below first side 14. A plurality of serrations 42 about 0.04 inch wide, about 0.02 inch deep and spaced about 0.07 inch apart may be formed in floor 40 to provide a gripping surface upon which the operator's thumb is retained during placement of platform 12 onto the skin of the test subject. However, it will be readily appreciated that other techniques may be used to provide a gripping surface on floor 40, such as, by way of example, scoring of floor 40 or inclusion of a plurality of dimples. Further, other structures may be used for thumb stop 26 (e.g., walls protruding above first side 14 spaced to receive the thumb of an operator) so long as they provide suitable means for retention of the operators thumb during placement of platform 12.

Grips 28 may consist of a plurality of serrations 44 formed in second opposing side 16 parallel to leading edge 36 about 0.03 inch wide, about 0.02 inch deep and spaced about 0.07 inch apart. Serrations 44 are formed in about the first 1 inch of second opposing side 16 behind leading edge 36. However, as with serrations 42 in groove 32, other techniques may be used to form grips 28, such as scoring or raised dimples. Further, the size and spacing of serrations 42, 44 may be changed as is necessary. Adhesive strip 30 consists of an adhesive material deposited on second opposing side 16 and is about 0.005 inch thick and extends forwardly from trailing edge 46 of platform 12 about 0.2 inch. Together, grips 28 and adhesive strip 30 cooperate to fix the skin of the test subject and prevent movement thereof during insertion of hollow needle 24 as will be described below.

To reduce the amount of material needed, a rectangular notch 47 may be formed in the first side 14 at leading edge 36. Notch 47 is about 0.3 inch long and about 0.06 inch deep. This eliminates unneeded material but does not weaken platform 12 or thumb stop 26

Figure 4:
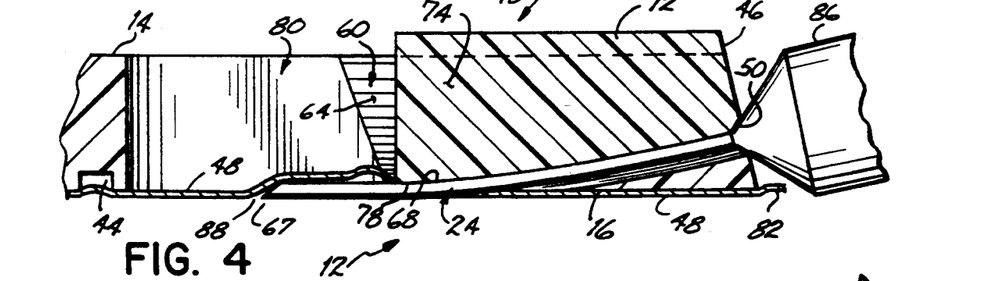
FIG. 4 is a cross-sectional view similar to FIG. 3 but with a tuberculin needle inserted fully within the guide channel.

Referring to FIGS. 3 and 4, channel inlet 20 is formed in and substantially perpendicular to trailing edge 46 about 0.08 inch above second opposing side 16. Trailing edge 46 extends upwardly and forwardly from second opposing side 16 at an angle of about 12 degrees to about 14 degrees from vertical and preferably of about 12 degrees from vertical. Thus, channel 18 initially extends forwardly from channel inlet 20 at an angle of about 12 degrees to about 14 degree relative to second opposing side 14 and preferably at an angle of about 12 degrees relative thereto. Extending forwardly from channel inlet 20, channel 18 follows a curvilinear trajectory consisting of an arcuate path that is convex relative to second opposing side 16 having a radius of curvature of about 1.8 inches. Channel 18 terminates in a substantially horizontal segment about 0.02 inch in length at channel outlet 22 which is positioned on second opposing side 16 about 0.3 inch forward of trailing edge 46. Thus, channel outlet 22 is at an angle of about 0 degrees to about 2 degrees relative to second opposing side 16 and preferably at about 0 degrees.

Hollow needle 24 is slidably receivable within channel 18 and, preferably, is flexible to permit it to assume the trajectory thereof. Thus, by forming channel 18 with the above: described curvilinear trajectory, hollow needle 24 is urged to follow the curvilinear trajectory. As needle 24 is inserted through channel 18, it enters the skin of the test subject at a shallow angle and pierces to a depth of about 0.002 inch, the thickness of the epidermis 48, and then follows a trajectory substantially parallel to epidermis 48 during the remainder of insertion of the needle (see FIG. 4). To assist the operator in initially inserting needle 24 into channel 18, channel inlet 20 has a counter sink 50 about 0.03 inch in diameter formed therein.

Figure 6:
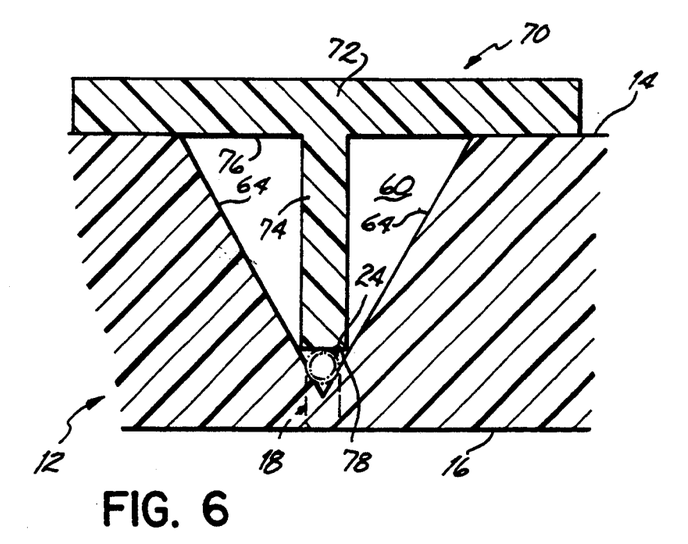
FIG. 6 is an enlarged partial cross-sectional view of the Mantoux tuberculin test device taken along line 6—6 of FIG. 3.
Figure 7:
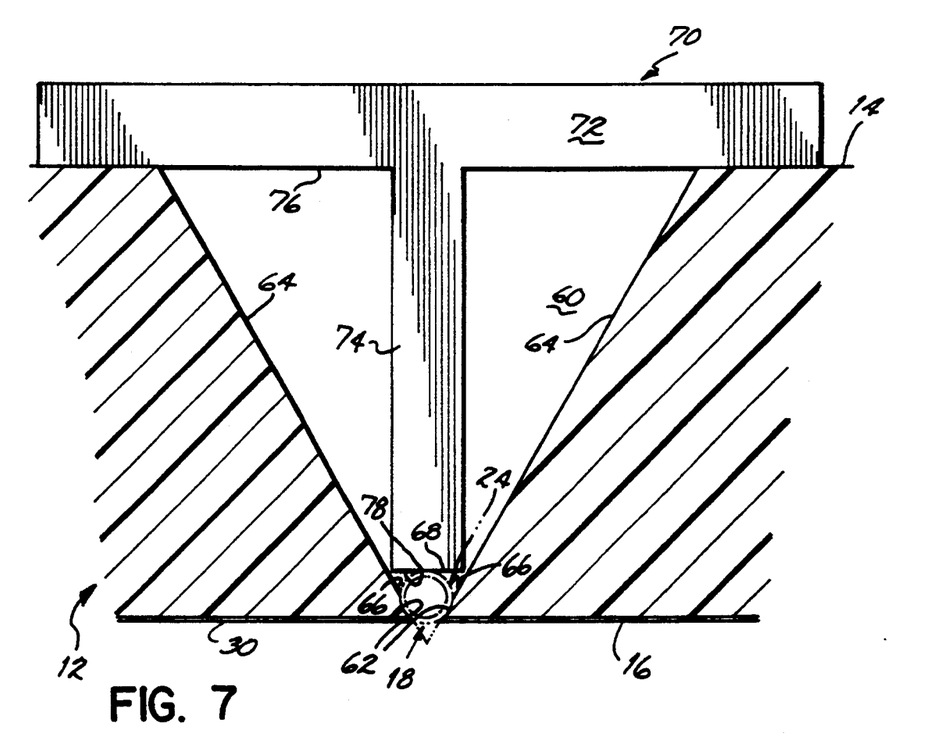
FIG. 7 is an enlarged partial cross-sectional view of the Mantoux tuberculin test device taken along line 7—7 of FIG. 3.

With reference to FIGS. 5-7, channel 18 may be formed by cutting or manufacturing a V-shaped notch 60 in first side 14 of platform 12. A second circular cut may be made to provide a circular base 62 substantially the same diameter as needle 24. Extending upward, and forming about a 60 degree angle therebetween, are sides 64. Together, circular base 62 and sides 64 form the lower portion 66 of channel 18. This V-shaped notch 60 and circular base 62 aid in guiding hollow needle 24 during insertion through channel 18. It also provides an open space to prevent the tip 67 of hollow needle 24 from impaling the wall of channel 18 as needle 24 is advanced therethrough. The roof 68 of channel 18 is formed by a T-shaped cap 70 having a horizontal component 72 and a vertical component 74. The lower surface 76 of horizontal component 72 rests on first side 14 and vertical component 74 is sized such that the lower edge 78 thereof parallels and is spaced about 0.014 inch to about 0.015 inch above the bottom of circular base 62. Thus, when hollow needle 24 is advanced through channel 18, it will rest on circular base 62 with only a point of contact with lower edge 78. This structure serves to minimize the friction between needle 24 and channel 18 during advancement of the needle. Additionally, cap 70 may be retained within V-shaped notch 60 by applying adhesive to the lower surface 76 of horizontal component 72 where it contacts first side 14 or by any other accepted technique. This method of manufacturing channel 18 has the advantage of being easy and cost effective. Further, it results in channel 18 being closely sized to that of hollow needle 24 thereby enabling tuberculin test device 10 to accurately and reliably guide hollow needle 24 during insertion. However, as will be readily apparent to those skilled in the art, other methods of manufacture may be used, such as, by way of example, injection molding test device 10 as one single piece, or molding V-shaped notch 60 in platform 12, and still result in the desired precision.

To permit the formation of a wheal on the surface of the skin of the test subject, platform 12 includes an oval slot 80 having a width of about 0.125 inch to about 0.25 inch and a length of about 0.25 inch to about 0.35 inch extending through platform 12. Slot 80 is centered about 0.4 to about 0.5 inch forward of trailing edge 46 such that it is in communication with channel outlet 22. Specifically, lower portion 66 of channel 18 exits through said second opposing side 16 and roof 68 of channel 18 exits into slot 80. Slot 80 permits the epidermis 48 to tent up above hollow needle 24 when it is inserted through channel 18 and into the skin 82 of the test subject. Additionally, as the tuberculin test material is injected under the epidermis 48, a wheal is formed on the skin surface and is received within slot 80. Still further, slot 80 is positioned such that when hollow needle 24 is fully inserted into channel 18, the tip 67 of hollow needle 24 is generally centered underneath slot 80 (see FIG. 4). Although slot 80 is shown as being oval, other shaped slots may be used such as circular or elliptical. Further, slot 80 need not extend entirely through platform 12, but rather, may be formed to extend only partially into platform 12 from second opposing side 16.

In use, second opposing side 16 of platform 12 is placed against the skin 82 of the test subject. The operator then pushes downwardly and forwardly (i.e., in the direction from channel inlet 20 to channel outlet 22) on thumb stop 26 by placement of the thumb against front wall 34 and groove floor 40. This causes grips 28 on second opposing side 16 to engage skin 82 and stretch it taut. The hollow needle 24 is then introduced into channel inlet 20 and inserted through channel 18 (alternatively, the user may insert hollow needle 24 partially into channel 18 prior to placement of platform 12 against the skin 82 of the test subject). As hollow needle 24 emerges from channel outlet 22 and contacts epidermis 48, adhesive strip 30 locks the skin, preventing it from being pushed into a wave ahead of needle tip 67. Upon entering epidermis 48, needle 24 is urged by channel 18 to follow a curvilinear trajectory such that it pierces the skin 82 to a depth just below the surface of epidermis 48, i.e., about 0.002 inch below the surface of the skin 82 (see FIG. 7). As the needle is inserted into the skin 82, the epidermis 48 tents over needle 24 and is pushed into slot 80 (see FIG. 4). After needle 24 is fully inserted into channel 18 such that hub 86 of hollow needle 24 contacts trailing edge 46, needle tip 67 is centrally positioned beneath slot 80 and just below epidermis 48 as indicated by 88 in FIG. 4. For a standard #27 regular bevel needle, needle 24 will travel about 0.09 inch under the skin when it is fully inserted. After hypodermic needle 24 has been fully inserted into channel 18, the tuberculin test material is then injected into the injection site and a wheal (not shown) is formed on skin 82 and into slot 80. Hollow needle 24 is then withdrawn and platform 12 is removed from the skin 82 of the test subject. Thus, in accordance with the principles of the present invention, tuberculin test device 10 permits an operator to administer a Mantoux tuberculin test quickly, easily and reliably.

Figure 8:
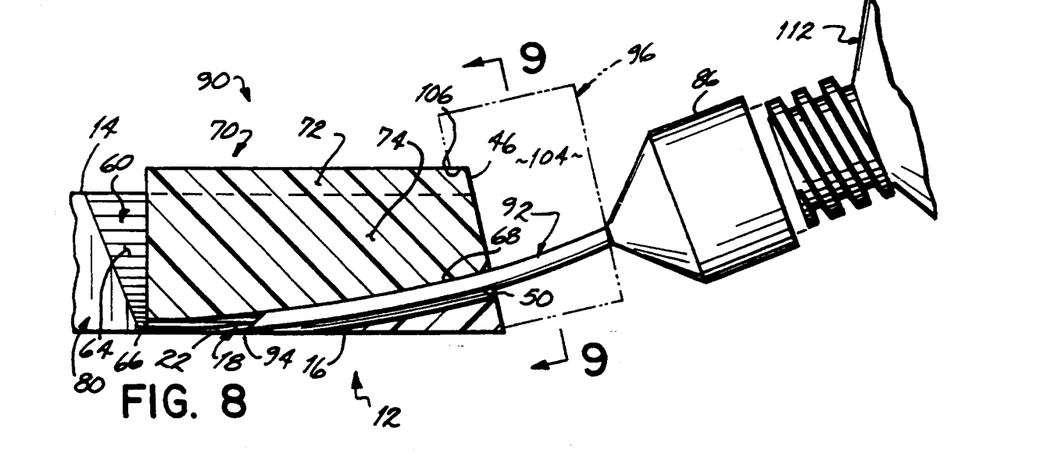
FIG. 8 is a cross-sectional view similar to FIG. 3 but of another device for administering a Mantoux tuberculin test in accordance with the principles of the present invention shown with a tuberculin needle retained within the guide channel.

With reference to FIG. 8, and in accordance with a further aspect of the invention, a tuberculin test device 90 made in accordance with the principles of the present invention may incorporate a hollow needle 92, such as a standard #27 regular bevel needle, within channel 18. To retain needle 92 within channel 18 and prevent the tip 94 of needle 92 from protruding beyond channel outlet 22 prior to use, a needle stop 96 is placed over needle 92 between needle hub 86 and trailing edge 46.

Figure 9:
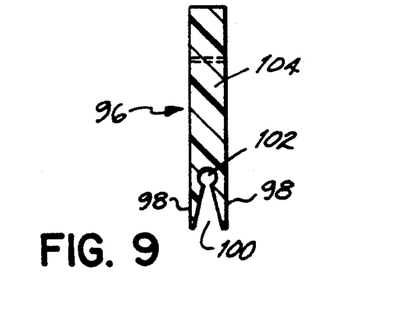
FIG. 9 is a front plan view of the needle stop for the Mantoux tuberculin test device of FIG. 8.

Referring to FIGS. 8 and 9, needle stop 96 is similar to a clothes-pin in that it includes a pair of opposed flexible fingers 98 forming an inverted V-shaped trough 100 therebetween. At the apex of V-shaped trough 100 is a circular groove 102 sized to releasably receive needle 24. Extending upwardly from fingers 98 is a generally rectangular body 104 and may include a notch 106 sized to rest upon trailing edge 46 and first side 14 of platform 12. Needle stop 96 may be of any length sufficient to prevent needle tip 94 from protruding beyond channel outlet 22 and will vary depending upon the needle 24 used.

Figure 10:
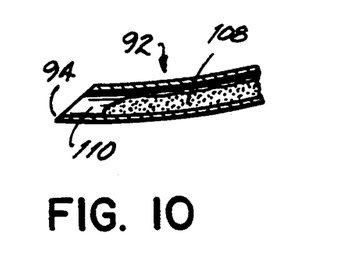
FIG. 10 is an enlarged partial cross-sectional view of a tuberculin needle having dry PPD deposited therein.

Incorporation of hollow needle 92 within channel 18 during the manufacturing process of tuberculin test device 90 has been found to be advantageous. Specifically, it eliminates the need for the operator to insert needle 92 into channel 18 before the injection. Additionally, it has been found beneficial to deposit the PPD tuberculin test material 108 within the lumen 110 of hollow needle 92 (see FIG. 10). The measured amount of dried PPD material 108 may be deposited during the manufacturing process by desiccating or freeze drying a concentrated PPD solution that was previously drawn into the needle. This amount corresponds, approximately, to the PPD coating of the tines in the present multi-prong tine test. By depositing the tuberculin test material, or other material that is to be injected, within the needle, the need for separately stocking and refrigerating the PPD test solutions is eliminated, thereby increasing the ease and cost of administering the tuberculin test in field conditions.

To use the alternative embodiment, the operator first attaches a syringe 112 containing about 0.1 cc of sterile PPD diluent, which does not require refrigeration, to hollow needle 92. The operator then removes needle stop 96 from needle 92 and places second opposing side 16 against the skin 82 of the test subject. As before, the operator pushes downwardly and forwardly on thumb stop 26, causing grips 28 to stretch the skin 82 taut. Hollow needle 92 is inserted into the skin 82, piercing to a depth of about 0.002 inch and traveling about 0.09 inch under epidermis 48. The 0.1 cc of sterile PPD diluent is then injected through needle 92, dissolving and flushing the PPD powder into the wheal formed at the injection site. Hollow needle 92 is then withdrawn from the skin 82 and the entire tuberculin test device 90 disposed of by any accepted method.

The tuberculin test device 10, 90 as disclosed has many applications in addition to use in administering a Mantoux tuberculin text. For example, by altering the dimensions and trajectory of channel 18, test device 10, 90 could be used for guiding the insertion of any sterile needle into the body at any prescribed angle, direction and depth for both the introduction or removal of fluids from the beady. Thus, a device made in accordance with the principles of the present invention may be used for any procedure where accurate insertion of a needle is desired.

By virtue of the foregoing, there is thus provided a Mantoux tuberculin test device that may easily, quickly and reliably be used for administering a Mantoux tuberculin test or for accurate insertion of any sterile hypodermic or other needle. While the present invention has been illustrated by description of two embodiments, it is not the intention of the applicant to restrict or limit the scope of the appended claims to such detail. For example, the dimensions and configuration of platform 12 may be altered depending upon the procedure to be formed and type of needle 24 to be used. Additionally, the trajectory followed by channel 18, and the location of channel inlet 20 and channel outlet 22, may be altered to provide different trajectories, angles of entry and depths of insertion of the needle. Further, additional advantages will readily appear to those skilled in the art; thus, the invention is not limited to the specific details, apparatus or method shown and described.

What is claimed is:

1. A device for guiding the insertion of a hollow needle into the body at a prescribed angle, direction and depth for the introduction or removal of fluids from the body comprising:

a platform having a first side and a second opposing side and a channel extending therethrough, said channel having an inlet and an outlet and being sized to receive and guide a hollow needle to guide the insertion of the hollow needle into the body for the introduction or removal of fluids;

a thumb stop on said first side of said platform; and gripping means on said platform second opposing side, said thumb stop and said gripping means cooperating to fix the skin of the test subject and prevent movement thereof during insertion of the needle.

2. The hollow needle guide of claim 1 wherein said gripping means include a plurality of serrations and an adhesive strip.

3. A device for guiding the insertion of a hollow needle into the body at a prescribed angle, direction and depth for the introduction or removal of fluids from the body comprising:

a platform having a first side and a second opposing side and a channel extending therethrough, said channel having an inlet and an outlet and being sized to receive and guide a flexible hollow needle to guide the insertion of the flexible hollow needle into the body for the introduction or removal of fluids, said channel following a curvilinear path to urge the flexible hollow needle into a curvilinear trajectory giving the needle a shallow angle of entry into the body.

4. The hollow needle guide of claim 3 further comprising a slot on said second opposing side of said platform, said slot being sized to allow tenting of the superficial layers of the skin and creation of a wheal above the skin surface when the flexible needle is inserted into the skin and fluid injected therethrough.

5. The hollow needle guide of claim 3 wherein said channel has a substantially inverted triangular cross-section to urge the tip of the flexible needle to travel along the lower apex of said channel.

6. The hollow needle guide of claim 4, wherein the hollow needle is a tuberculin needle, said platform is a rigid plate having a length of about 1.5 to about 1.8 inches, a width of about 0.625 to about 0.75 inch and a thickness of about 0.1 to about 0.125 inch, said slot being in communication with said channel outlet and having a width of about 0.125 to about 0.25 inch and a length of about 0.25 to about 0.35 inch and said channel extends forwardly from said channel inlet at an angle of about 12 to about 14 degrees relative to said second opposing side, extends rearwardly from said channel outlet at an angle of about 0 to about 2 degrees relative to said second opposing side and follows a substantially arcuate path from said channel inlet that is convex relative to said second opposing side having a radius of curvature of about 1.8 inches terminating at said channel outlet in a substantially horizontal segment about 0.02 inch in length to urge the tuberculin needle to enter the skin to a depth of about 0.001 to about 0.002 inch and to travel a length of about 0.09 to about 0.125 inch under the skin when the needle is fully inserted into said needle guide.

7. The hollow needle guide of claim 6 wherein said rigid plate is about 1.8 inches long, about 0.6 inch wide and about 0.1 inch thick, said slot extends through said plate and is generally oval having a length of about 0.25 inch and a width of about 0.125 inch and said channels extends forwardly from said channel inlet at an angle of about 12 degrees relative to said second opposing side, extends rearwardly from said channel outlet at an angle of about 0 degrees relative to said second opposing side and follows a substantially arcuate path from said channel inlet having a radius of curvature of about 1.8 inches terminating at said channel outlet in a substantially horizontal segment about 0.02 inch in length to urge the tuberculin needle to enter the skin to a depth of about 0.002 inch and travel a length of about 0.09 inch under the skin when the needle is fully inserted into said needle guide.

8. The hollow needle guide of claim 3 wherein said platform is plastic.

9. A device for guiding the insertion of a hollow needle into the body at a prescribed angle, direction and depth for the introduction or removal of fluids from the body comprising:
   a platform having a first side and a second opposing side and a channel extending therethrough, said channel having an inlet and an outlet and being sized to receive and guide a hollow needle to guide the insertion of the hollow needle into the body for the introduction or removal of fluids;
   a hollow needle having a tip and hub thereon positioned within said channel; and
   a needle stop releasably secured to said needle between said hub and said platform sized to prevent said needle tip from protruding beyond said channel outlet until said needle is connected to a syringe for use.

10. The hollow needle guide of claim 9 further comprising a dry substance deposited on the inner surface of said hollow needle to be flushed into the injection site when a syringe having diluent therein is secured to said needle and the diluent is injected through said needle.

11. The hollow needle guide of claim 10 wherein said hollow needle is a hypodermic or tuberculin needle and said dry substance is PPD.

12. An intradermal tuberculin test injection device for easy and accurate introduction of tuberculin test material beneath the epidermis of the skin comprising:
   a platform having a first side and a second opposing side;
   said platform having a channel extending therethrough, said channel having an inlet and an outlet and being sized to receive and guide a flexible hypodermic or tuberculin needle;
   a slot in said platform second opposing side sized to permit creation of a wheal above the skin surface following injection of the tuberculin test material;
   a thumb stop in said platform first side sized to receive the thumb of an operator to assist in positioning said injection device; and
   gripping means on said platform second opposing side to grip the skin of the test subject and prevent movement thereof during insertion of the hypodermic or tuberculin needle.

13. The injection device of claim 12 wherein said channel follows a curvilinear path to urge the flexible tuberculin needle into a curvilinear trajectory giving the needle a shallow angle of entry into the body.

14. The injection device of claim 13 wherein said gripping means include a plurality of serrations and an adhesive strip.

15. The injection device of claim 13 wherein said channel has a substantially inverted triangular cross-section to urge the tip of the flexible hypodermic or tuberculin needle to travel along the lower apex of said channel without impinging on the surface of said channel.

16. The injection device of claim 13 wherein said platform is a rigid rectangular plate having a length of about 1.5 to about 1.8 inches, a width of about 0.625 to about 0.75 inch and a thickness of about 0.1 to about 0.125 inch, said slot being in communication with said channel outlet and having a width of about 0.125 to about 0.25 inch and a length of about 0.25 to about 0.35 inch and said channel extends forwardly from said channel inlet at an angle of about 12 to about 14 degrees relative to said second opposing side, extends rearwardly from said channel outlet at an angle of about 0 to about 2 degrees relative to said second opposing side and follows a substantially arcuate path frown said channel inlet that is convex relative to said second opposite face having a radius of curvature of about 1.8 inches terminating at said channel outlet in a substantially horizontal segment about 0.02 inch in length to urge the tuberculin needle to enter the skin to a depth of about 0.001 to about 0.002 inch and travel a length of about 0.09 to about 0.125 inch under the skin when the needle is fully inserted into said injection device.

17. The injection device of claim 16 wherein said rigid rectangular plate is about 1.8 inches long, about 0.6 inch wide and about 0.1 inch thick, said slot extends through said plate and is generally oval having a length of about 0.25 inch and a width of about 0.125 inch and said channel extends forwardly from said channel inlet at an angle of about 12 degrees relative to said second opposing side, extends rearwardly from said channel outlet at an angle of about 0 degrees relative to said second opposing side and follows a substantially arcuate path from said channel inlet having a radius of curvature of about 1.8 inches terminating at said channel outlet in a substantially horizontal segment about 0.02 inch in length to urge the tuberculin needle to enter the skin to a depth of about 0.002 inches and travel a length of about 0.09 inch under the skin when the needle is fully inserted into said injection device.

18. The injection device of claim 13 wherein said platform is plastic.

19. A disposable system for easily and accurately administering a Mantoux tuberculin test comprising:
   a platform having a first side and a second opposing side;
   said platform having a channel extending therethrough, said channel having an inlet and an outlet and being sized to receive and guide a flexible tuberculin needle;

a slot in said platform second opposing side sized to permit creation of a wheal above the skin surface following injection of the tuberculin test material;

a thumb stop in said platform first side sized to receive the thumb of an operator to assist in positioning said injection device;

gripping means on said platform second opposing side to grip the skin of the test subject and prevent movement thereof during insertion of the tuberculin needle;

a hollow flexible hypodermic or tuberculin needle having a tip and hub thereon positioned within and advanceable through said channel; and a needle stop releasably secured to said needle between said hub and said platform sized to prevent said needle tip from protruding beyond said channel outlet until said needle is connected to a syringe for use.

20. The disposable system of claim 19 wherein said channel follows a curvilinear path to urge the flexible hypodermic or tuberculin needle into a curvilinear trajectory giving the needle a shallow angle of entry into the body.

21. The disposable system of claim 20 wherein said gripping means include a plurality of serrations and an adhesive strip, 22. The disposable system of claim 20 wherein said channel has a substantially inverted triangular cross-section to urge the tip of the flexible needle to travel along the lower apex of said channel without impinging in the surface of said channel.

23. The disposable system of claim 20 wherein said platform is a rigid rectangular plate having a length of about 1.5 to about 1.8 inch, a width of about 0.625 to about 0.75 inch and a thickness of about 0.1 to about 0.125 inch, said slot being in communication with said channel outlet and having a width of about 0.125 to about 0.25 inch and a thickness of about 0.25 to about 0.35 inch and said channel extends forwardly from said channel inlet at an angle of about 12 to about 14 degrees relative to said second opposing side, extends rearwardly from said channel outlet at an angle of about 0 to about 2 degrees relative to said second opposing side and follows a substantially arcuate path from said channel inlet that is convex relative to said second opposite face having a radius of curvature of about 1.8 inches terminating at said channel outlet in a substantially horizontal segment about 0.02 inch in length to urge the tuberculin needle to enter the skin to a depth of about 0.001 to about 0.002 inch and travel a length of about 0.09 to about 0.125 inch under the skin when the needle is fully advanced through said channel.

24. The disposable system of claim 20 wherein said rigid rectangular plate is about 1.8 inches long, about 0.6 inch wide and about 0.1 inch thick, said slot extends through said plate and is generally oval having a length of about 0.25 inch and a width of about 0.125 inch and said channel extends forwardly from said channel inlet at an angle of about 12 degrees relative to said second opposing side, extends rearwardly from said channel outlet at an angle of about 0 degrees relative to said second opposing side and follows a substantially arcuate path from said channel inlet having a radius of curvature of about 1.8 inches terminating at said channel outlet in a substantially horizontal segment about 0.02 inch in length to urge the tuberculin needle to enter the skin to a depth of about 0.002 inch and travel a length of about 0.09 inch under the skin when the needle is fully advanced through said channel.

25. The disposable system of claim 19 further comprising a measured amount of dry PPD deposited within said hollow hypodermic or tuberculin needle, said dry PPD being flushed from said needle and into the injection site when a syringe having diluent therein is attached to said needle and the diluent forced through said needle.

26. The hollow needle guide of claim 19 wherein said platform is plastic.

27. A method of quickly and easily administering a Mantoux tuberculin test comprising:

providing a platform having a channel therethrough sized to receive and guide a flexible tuberculin needle;

positioning said platform on the inner aspect of the test subject's forearm;

introducing a flexible tuberculin needle into said channel;

inserting said needle through said channel and into the skin of the test subject;

injecting tuberculin test material through said needle and into the injection site;

withdrawing said needle; and removing said platform from the test subject's arm.

28. The method of administering a Mantoux test of claim 27 wherein said channel follows a curvilinear path to urge said flexible hypodermic or tuberculin needle into a curvilinear trajectory giving said needle a shallow angle of entry into the body.

29. The method of administering a Mantoux test of claim 28 wherein said platform is a rigid plate having top and bottom surfaces, a thumb stop on said top surface sized to receive the thumb of an operator, gripping means on said bottom surface and a slot extending through said plate sized to permit formation of a wheal above the skin surface at the test site.

30. The method for administering a Mantoux test of claim 29 further comprising continuing insertion of said needle until the hub thereof contacts said platform to position the needle under said slot and about 0.002 inch beneath the surface of the skin.

31. The method of administering a Mantoux test of claim 29 wherein positioning said platform on the forearm includes:

placing said bottom surface of said plate on the inner aspect of the test subject's forearm; and applying a downward and forward pressure to said plate at said thumb stop such that said gripping means engage and pull taut the skin of the test subject to prevent buckling of the skin when said needle is inserted therein.

32. The method of administering a Mantoux test of claim 29 wherein said gripping means include a plurality of serrations and an adhesive grip.

33. A method of quickly and easily administering a Mantoux tuberculin test comprising:

providing a platform having a channel therethrough with an inlet and an outlet sized to receive and guide a hypodermic or tuberculin needle, said channel having a flexible hypodermic or tuberculin needle therein, the hub of said needle extending beyond said inlet, and a needle stop on said needle between said hub and said platform to retain said needle within said channel and to prevent protrusion of the tip of said needle beyond said channel outlet;

attaching a syringe to said hub of said needle;
removing said needle stop from said needle;
positioning said platform on the inner aspect of the test subject's forearm;
advancing said needle through said channel for insertion into the skin of the test subject;
injecting tuberculin test material into the injection site;
withdrawing said needle from the skin of the test subject; and
removing said platform from the test subject's arm.

34. The method of administering a Mantoux test of claim 33 wherein said channel follows a curvilinear path to urge said flexible hypodermic or tuberculin needle into a curvilinear trajectory giving said needle a shallow angle of entry into the body.

35. The method of administering a Mantoux test of claim 34 wherein said platform is a rigid plate having top and bottom surfaces, a thumb stop on said top surface sized to receive the thumb of an operator, gripping means on said bottom surface and a slot extending through said plate sized to permit formation of a wheal above the skin surface at the test site.

36. The method for administering a Mantoux test of claim 35 further comprising continuing insertion of said needle until the hub thereof contacts said platform to position the needle under said slot and about 0.002 inch beneath the surface of the skin.

37. The method of administering a Mantoux test of claim 35 wherein positioning said platform on the forearm includes:
 placing said bottom surface of said plate on the inner aspect of the test subject's forearm; and
 applying a downward and forward pressure to said plate at said thumb stop such that said gripping means engage and pull taut the skin of the test subject to prevent buckling of the skin when said needle is inserted therein.

38. The method of administering a Mantoux test of claim 35 wherein said gripping means include a plurality of serrations and an adhesive grip.

39. The method of administering a Mantoux test of claim 33 wherein the syringe has diluent therein and said needle contains a measured amount of dry PPD that is flushed into the injection site when the diluent is forced through said needle.

* * * * *

UNITED STATES PATENT AND TRADEMARK OFFICE
CERTIFICATE OF CORRECTION

PATENT NO. : 5,437,640
DATED : August 1, 1995
INVENTOR(S) : Louis Schwab

It is certified that error appears in the above-indentified patent and that said Letters Patent is hereby corrected as shown below:

Column 1, Line 28, "fir" should be --for--.

Column 2, Line 50, "be," should be --be-- (delete the comma).

Column 4, Line 31, "from from" should be --from front--.

Column 5, Line 9, "14 degree" should be --14 degrees--.

Column 5, Line 25, "above:" should be --above-- (delete the colon).

Column 7, Line 23, "before the injection. Additionally". The word "Additionally" should begin a new paragraph.

UNITED STATES PATENT AND TRADEMARK OFFICE
CERTIFICATE OF CORRECTION

PATENT NO. : 5,437,640
DATED : August 1, 1995
INVENTOR(S) : Louis Schwab

It is certified that error appears in the above-indentified patent and that said Letters Patent is hereby corrected as shown below:

Column 7, Line 61, "beady" should be --body--.

Column 10, Line 33, "frown" should be --from--.

Signed and Sealed this

Nineteenth Day of December, 1995

Attest:

BRUCE LEHMAN

Attesting Officer

Commissioner of Patents and Trademarks